United States Patent
Viaud et al.

(10) Patent No.: US 7,603,031 B1
(45) Date of Patent: Oct. 13, 2009

(54) PROGRAMMABLE, MULTI-SPECTRAL, IMAGE-CAPTURE ENVIRONMENT

(75) Inventors: George Viaud, Little Falls, NJ (US); Ken Budris, Mahwah, NJ (US); Doug Canfield, Mountain Lakes, NJ (US); Dennis DaSilva, Wanaque, NJ (US); Jim Dornbusch, Califon, NJ (US); John Robinson, Point Pleasant, NJ (US)

(73) Assignee: Canfield Scientific, Incorporated, Fairfield, NJ (US)

( * ) Notice: Subject to any disclaimer, the term of this patent is extended or adjusted under 35 U.S.C. 154(b) by 718 days.

(21) Appl. No.: 11/167,540

(22) Filed: Jun. 27, 2005

Related U.S. Application Data

(60) Provisional application No. 60/636,197, filed on Dec. 15, 2004.

(51) Int. Cl.
 *G03B 15/03* (2006.01)
 *H04N 5/222* (2006.01)
 *A61B 6/00* (2006.01)

(52) U.S. Cl. .................. 396/159; 348/371; 600/476

(58) Field of Classification Search .................. 396/2, 396/14, 155, 159, 173, 182; 348/371
See application file for complete search history.

(56) References Cited

U.S. PATENT DOCUMENTS

| | | | |
|---|---|---|---|
| 3,952,320 A | 4/1976 | Blount | |
| 4,035,814 A | 7/1977 | Mobusawa | |
| 4,132,923 A | 1/1979 | Gahler et al. | |
| 4,164,686 A | 8/1979 | Vital et al. | |
| 4,334,856 A | 6/1982 | Broadt et al. | |
| 4,379,983 A | 4/1983 | Takematsu | |
| 4,441,797 A | 4/1984 | Maruyama et al. | |
| 4,509,844 A | 4/1985 | Takematsu | |
| 4,523,830 A | 6/1985 | Iida et al. | |
| 4,954,861 A | 9/1990 | Nagaoka et al. | |
| 5,019,845 A | 5/1991 | Asakura et al. | |
| 6,151,073 A | 11/2000 | Steinberg et al. | |
| 6,498,901 B2 | 12/2002 | Kawasaki et al. | |
| 6,571,003 B1 | 5/2003 | Hillebrand et al. | |

(Continued)

OTHER PUBLICATIONS

K. Miyamoto et al., "The Beauty Imaging System: For the Objective Evaluation of Skin Condition," Journal of Cosmetic Science, vol. 53, No. 1, Jan./Feb. 2002.
Canfield Scientific, Visia Complexion Analysis System, Brochure 0801-18.

(Continued)

*Primary Examiner*—Patrick J. Assouad
*Assistant Examiner*—Autumn Parker
(74) *Attorney, Agent, or Firm*—Brosemer, Kolefas & Assoc. LLC

(57) ABSTRACT

A multi-flash photography system provides a dynamically-configurable lighting environment for a single exposure that is created and shaped through the sequentially firing of various light sources with different lighting characteristics controlled in accordance with both a programmed template specifying the flash type, position, firing order, and output intensity, as well as optical processing requirements such as filtering, polarizing, etc., and a shared photometric detector located sufficiently close to the subject being photographed to ensure that the light seen by the detector is substantially the same as the light received at the subject.

21 Claims, 6 Drawing Sheets

U.S. PATENT DOCUMENTS

| | | | |
|---|---|---|---|
| 2004/0125996 A1 | 7/2004 | Eddowes et al. | |
| 2004/0179832 A1* | 9/2004 | Okabe | 396/157 |
| 2004/0263678 A1* | 12/2004 | Kawakami | 348/371 |
| 2005/0030416 A1* | 2/2005 | Kametani et al. | 348/370 |
| 2005/0046739 A1* | 3/2005 | Voss et al. | 348/371 |
| 2005/0195316 A1* | 9/2005 | Kollias et al. | 348/370 |
| 2007/0212038 A1* | 9/2007 | Asai et al. | 396/14 |

OTHER PUBLICATIONS

Canfield Imaging Systems, "Taking standard and UV photographs with the Reflec system," CCS98008-5, Apr. 2001.

K. Miyamoto et al., "Development of a digital imaging system for objective measurement of hyperpigmented spots on the face," Skin Research and Tech., vol. 8, Issue 4, p. 227, Nov. 2002.

* cited by examiner

PROGRAMMABLE, MULTI-SPECTRAL, IMAGE-CAPTURE ENVIRONMENT

CROSS REFERENCE TO RELATED APPLICATION

This application claims the benefit of U.S. Provisional Patent Application No. 60/636,197, filed Dec. 15, 2004.

BACKGROUND OF THE INVENTION

1. Field of the Invention

The present invention relates to multi-flash photography and other image capture systems. More specifically, the invention provides a photography system wherein the lighting environment for a single exposure is created and shaped through the sequentially firing of various flash devices with different lighting characteristics controlled in accordance with both a programmed template and a shared photometric detector located near the subject being photographed.

2. Description of the Related Art

Various types of multi-flash photography systems in which the amount of light of the main flash unit discharge is controlled in accordance with photometric reading taken from reflected light from either the entire or different areas of the subject (or a scene/object) at a pre-flash emission stage that is emitted before the main flash discharge are known in the art. In these conventional multi-flash photography systems, one or a plurality of flash devices are activated to emit a preflash, which is used to calculate the light output required during the main flash discharge. These calculations are very complicated because various settings (illumination angle setting, subject distance setting, guide number, etc.) are generally different between/amongst the other flash devices.

Light metering is traditionally done either at the flash unit itself or through-the-lens multi-segment photo-metering elements built within the camera.

P&G's Olay Beauty Imaging System disclosed in U.S. Pat. No. 6,571,003 and an article by Miyamoto and Hillebrand titled "The Beauty Imaging System: For the Objective Evaluation of Skin Condition" appearing in the Journal of Cosmetic Science, pages 62-65, January-February Edition 2002, and Canfield Scientifics' own REFLEC UV Instant Camera System and VISIA Complexion Analysis System use both visible and UV lighting to enhance various attributes of the skin. Canfield also sells cross- and parallel-polarizing filter kits to enhance other attributes of the skin during image capture.

Unilever has disclosed in US patent application 2004/0125996 a method and apparatus that uses multiple wavelength light sources to capture a multiple images, each under a single lighting modality during image capture used to diagnose skin conditions.

Despite the aforementioned advances in the art, there remains a need for being able to precisely customize the lighting characteristics (spectral content, light polarity, directionality, etc.) as well as the intensity composition of the lighting environment at the subject being photographed ensuring reproducible image-to-image capture in such demanding applications as for clinical/medical research. Moreover, the system needs to be able to dynamically create this lighting environment during each exposure of a rapid burst-mode image capture sequence to minimize subject movement that would otherwise compromise the ability for accurate cross-comparison of images.

SUMMARY OF THE INVENTION

The present invention provides a multi-flash photography system, wherein the lighting environment for a single exposure is created and shaped through the sequential firing of various flash devices with different lighting characteristics (spectral filtering, polarization, etc.) controlled in accordance with both a programmed template (specifying the flash type, position, firing order, and output intensity) and a shared photometric detector located sufficiently close to the subject being photographed to ensure that the light seen by the detector is proportionally the same as the light received by the subject.

The invention includes at least one light source, and more preferably multiple light sources, that may be flash sources such as xenon tubes, pulsed-light sources such as light emitting diodes, or continuous-light sources, such as fluorescent, halogen, and tungsten. The light sources may be used in conjunction with a filter mechanism such as a fixed filter or a filter wheel. The filter mechanism permits the apparatus designer or photographer to select a desired filter for each light source, for example, filters that provide linear, cross, parallel, or circular polarization, and/or pass ultra-violet, infrared, or another selected portion(s) of the light spectrum.

A camera is preferably centrally located with respect to the light sources. A filter mechanism may be placed in front of the lens of the camera instead of or in addition to the filter mechanisms for the individual light sources. In the preferred embodiments, multiple light sources have fixed optical filters located in their output path, while a filter wheel, consisting of rotary selectable array of optical filters, is located in front of the camera lens.

A control circuit may be provided for controlling the camera, the individual light sources, and any of the multi-filter mechanism(s), which may be implemented. The lighting characteristics of each photograph may be controlled by programming the control circuits to place the appropriate filter in front of each light source and/or the camera lens, actuate the individual light sources desired for the photograph in a specified sequence and/or with a specified timing with respect to each other, and to shut off each individual light source when the light output from that source reaches a preselected amount. Preferred embodiments of the control circuit may be programmed to take multiple photographs with multiple lighting combinations, in what is known as burst mode photography.

A sensor may be provided for monitoring the light output of the individual light sources, and providing appropriate signals to the control circuit to cut-off power to each light source at the appropriate time. Preferably, a single sensor assembly is used, and is positioned sufficiently close to the photographic subject or target so that light seen by the sensor is substantially the same as light seen on the target. One or more sensors may be contained within the sensor assembly.

Some embodiments of the invention may include an enclosure structured to enshroud the light sources, filter mechanism, and the lens of the camera. Some preferred enclosures are structured to accept a human face, other human body part, or other desired photographic subjects or targets.

It is therefore an object of the present invention to precisely create and shape the lighting environment during a single-image exposure consisting of a plurality of different spatially-separated flash or pulsed-light source to be fired in a preprogrammed sequence, potentially complemented with fixed light sources, wherein the spectral content, intensity, and duration are specified for each lighting event of the specified sequence.

It is another object of the invention to provide for the customization of lighting characteristics to enhance the specific attributes of the subject to be analyzed, permitting the selective use of xenon flash or other pulsed-light source potentially complemented with one or more continuous-light sources and optical/spectral processing such as wavelength band filtering (UV, infrared, etc.), and light polarity (linear, cross, parallel, or circular). Further enhancement of the attribute is possible through control of the lighting directionality, achieved by selecting the appropriately positioned light source, and specifying its firing sequence, and output intensity to achieve the desired effect ranging from very soft indirect, and diffused to hard and directional lighting.

It is a further object of the invention to provide a single photometric sensor to quantitatively meter and control the output of each flash/light source, thereby ensuring consistent light metering amongst the various sources, eliminating the potential for any differences due to inter-sensor variability, and providing a cost effective means over the alternative implementation of separate sources having a dedicated photometric sensor associated with each flash/light source that would implement a totally non-image-related metering mode and potentially cross contaminate each other.

It is another object of the invention to provide a single photometric sensor disposed near the subject being photographed, thereby ensuring the accurate measurement of the actual light that will be received at the subject as opposed to reflected light that has been the prior art (whether that light is measured by the flash unit itself or in conjunction with a camera's Through The Lens [TTL] metering system).

It is a further object of the invention to support rapid, burst image capture, wherein the lighting characteristics for each image in the capture sequence can be created and shaped according to a programmable shooting template, thereby helping to minimize subject movement image-to-image in the capture sequence, critical for cross image-comparison purposes.

These and other objects of the invention will become more apparent through the following description and drawings.

BRIEF DESCRIPTION OF THE DRAWINGS

Like reference characters denote like elements throughout the drawings.

DETAILED DESCRIPTION OF THE PREFERRED EMBODIMENTS

The present invention provides an apparatus and method for creating a programmable, multi-spectral flash environment.

Figure 1:
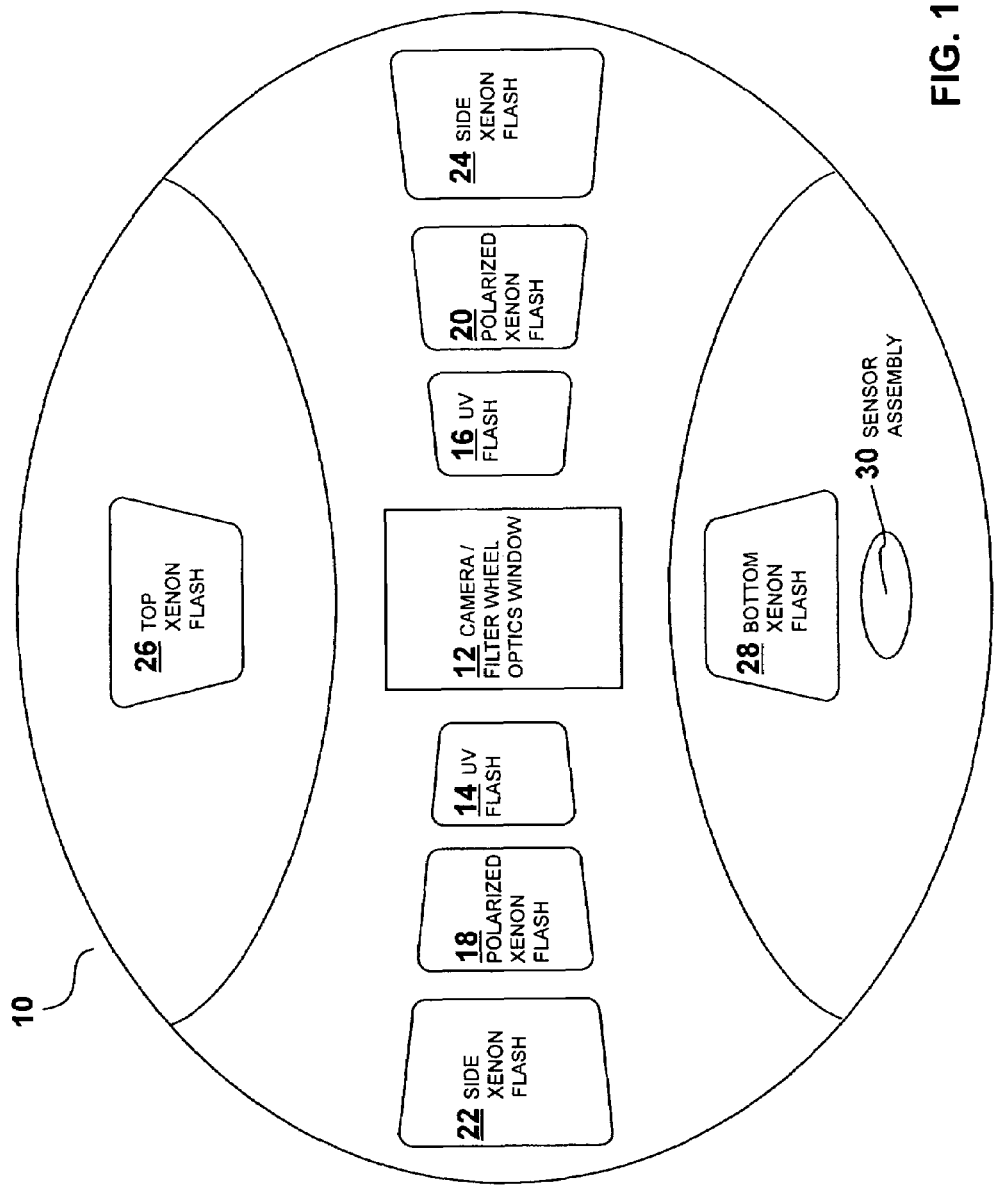
FIG. 1 is diagrammatic view of the equipment set according to one possible embodiment of the present invention.
Figure 2:
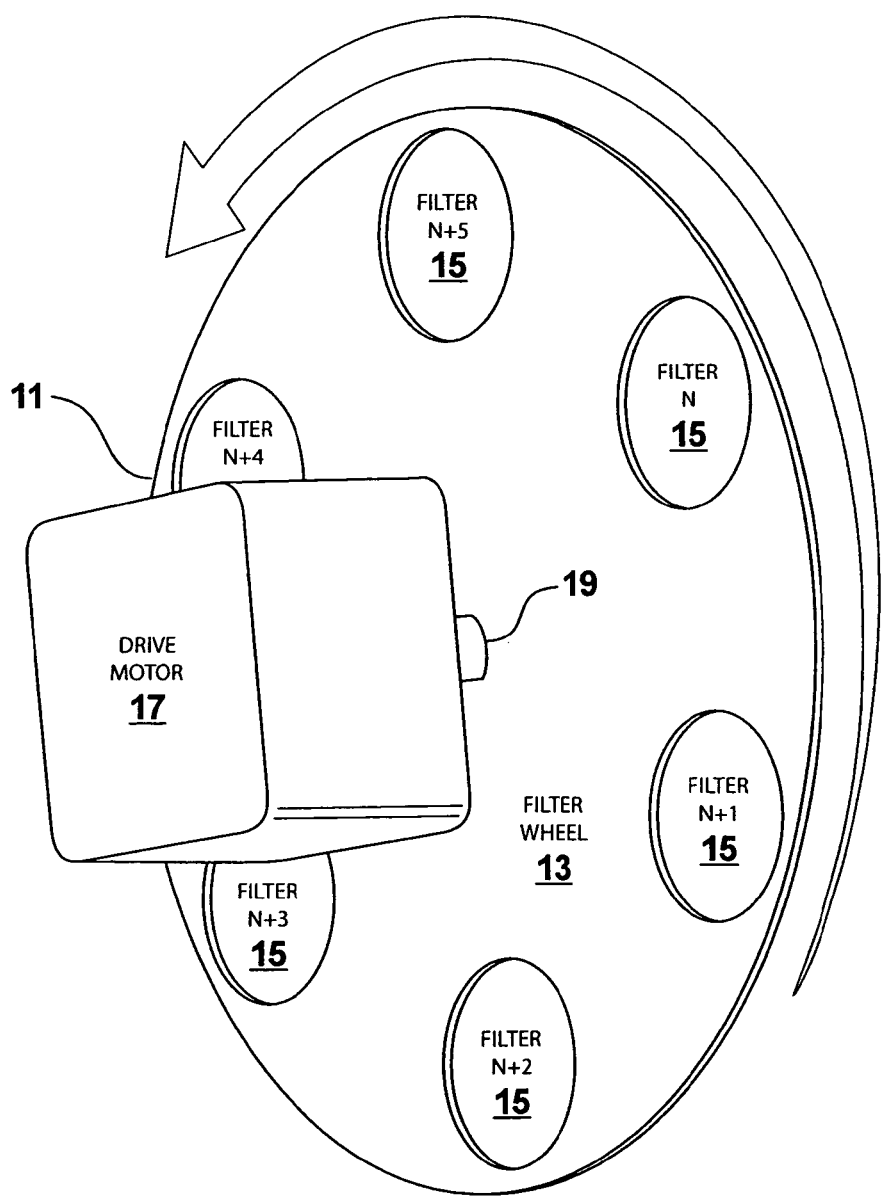
FIG. 2 is an isometric back view of a filter wheel that may be used with the present invention.

FIG. 1 illustrates one embodiment of the flash environment 10 that is particularly suited for medical and cosmetic facial photography. The flash environment 10 may include a centrally-mounted camera optics window 12 which, as is well-known to those skilled in the art, will have the camera lens and filter mechanism, such as a filter wheel, located directly behind it. Referring briefly to FIG. 2, a filter wheel 11 is illustrated. The filter wheel 11 includes a wheel 13 having a plurality of filters 15 disposed about its periphery. The wheel 13 is rotated by a drive motor 17 connected to the center of the wheel 13 by a drive shaft 19. Referring back to FIG. 1, a pair of ultraviolet flashes 14,16, using xenon tubes covered by ultraviolet filters, may be located on either side of the camera optics window 12. Continuing to move outward from either side of the camera optics window 12, a pair of polarized xenon flashes 18,20 may be located just outside of the ultraviolet flashes 14,16. Continuing outward to the sides of the flash environment 10, a pair of side xenon flashes 22,24 may be located outward of the polarized xenon flashes 18,20. Top xenon flash 26 and bottom xenon flash 28 may be located above and below the camera optics window 12, respectively. A sensor assembly 30 is disposed within the flash environment 10, preferably in a location that is in sufficiently close proximity to the subject being photographed so that the light hitting the sensor assembly 30 will be substantially the same as the light hitting the subject. Many alternative arrangements of light sources may be utilized in addition to the above. In another alternative embodiment, the flashes 14-28 may each be equipped with a filter mechanism such as a filter wheel, so that any of the flashes 14-28 may be utilized in conjunction with one or more filters that provide polarization (e.g., linear, cross, parallel, or circular), and/or spectral filtering (e.g., ultra-violet, infrared, or another selected portion(s) of the light spectrum.

High-precision medical and scientific photography can benefit from a flash system capable of using a variety of different flashes capable of providing light having different characteristics, some of which will flash in a predetermined sequence and/or combination to produce an image having desired characteristics, thereby enhancing the visibility of desired features within the photograph. The use of flashes, pulsed-light sources, and/or continuous-light sources with different lighting characteristics can be individually controlled to provide varying light output levels and a wide range of spectral modalities, as well as achieve specific lighting characteristics through optical processing (filtering, polarization, etc.) and directionality control that can be varied from very soft diffuse light to hard directional lighting. The location of the various flashes is tuned to the booth-shape and camera design, and will differ for other booth shape designs and camera configurations. Xenon flashes may be utilized when consistent full spectrum lighting is desired. Ultraviolet flashes are utilized to enhance mottled hyper-pigmentation that is associated with skin damage from sunlight. Parallel-polarized flashes are used to enhance attributes of surface topology, for example, flakiness. A cross-polarized flash is used to enhance subsurface features such as vascular details, pigmentation, and infiltrates. Infrared flashes are used to enhance the viewing of skin topology by correcting for shadowing and other limitations inherent with other spectrum lighting. Other types of lighting sources that may be utilized include pulsed-light sources (for example, light emitting diodes) and continuous-light sources (for example, incandescent, fluorescent, halogen, tungsten, etc.). Filters and other polarization devices may be placed in the optical path to further define the spectral characteristics of the light environment.

The sensor 30 may be operatively connected to any of several different metering circuits, with a particularly preferred metering circuit being disclosed in our copending patent application entitled "Light Metering Circuit for a Camera Flash." filed Dec. 15, 2004. Alternatively, other presently available metering circuits, for example, the one disclosed in U.S. Pat. No. 6,151,073, issued to Steinberg et al., on Nov. 21, 2000, may be used.

Figure 3:
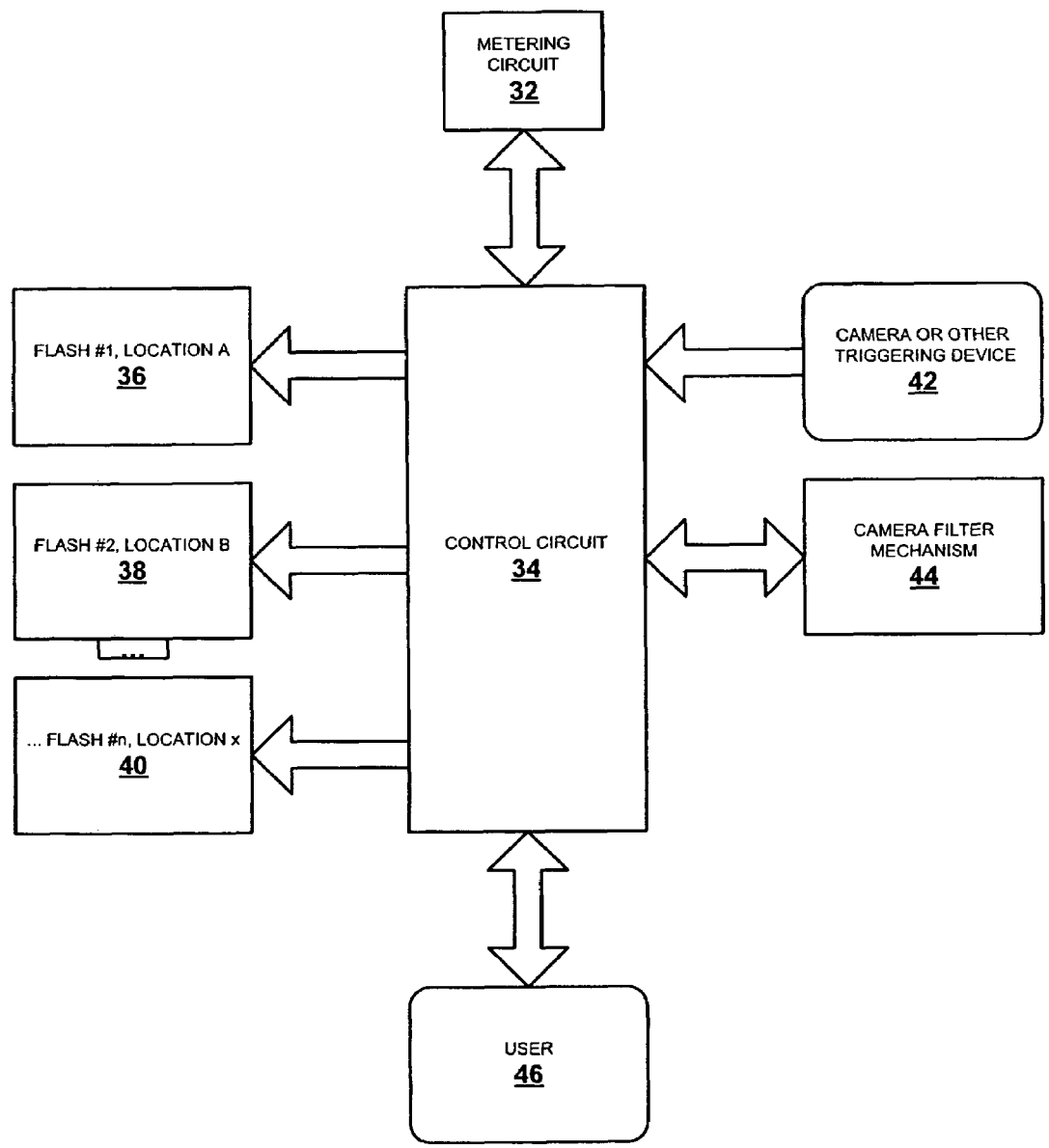
FIG. 3 is a schematic diagram showing subsections of the invention and their connectivity to each other and interface to the user.

Referring to FIG. 3, the interaction of the various components of the flash environment 10 is illustrated. The metering circuit 32 is connected to the control circuit 34. This connection is bi-directional allowing for control of the metering circuit 32 to be performed by the control circuit 34 and for metering information to be provided to the control circuit 34 by the metering circuit 32. A multitude of flashes, of which only three, 36,38,40, are shown in the illustrated embodiment, are attached to the control circuit 34. The connection is unidirectional allowing the flashes 36,38,40 to be controlled by the control circuit 34. A camera 42 or other triggering device is attached to the control circuit 34. This connection is unidirectional allowing for the camera 42 or other triggering device to signal the control circuit 34. This signal orders the control circuit 34 to fire the currently programmed flash sequence. The camera filter mechanism 44 is attached to the control circuit 34. This connection is bi-directional allowing for the filter mechanism 44 to be operated by the control circuit 34, as well as the transmittal of positioning information back to the control circuit 34. The user 46 interfaces with the control circuit 34, usually via control software in a bi-directional means. This allows the user 46 to give commands to the control circuit 34 such as setting a particular flash's intensity or setting the position of the filter mechanism 44. It also allows the control circuit 34 to communicate with the user (e.g., report to the user a sequence was fired successfully or to acknowledge a command being received successfully).

Figure 4:
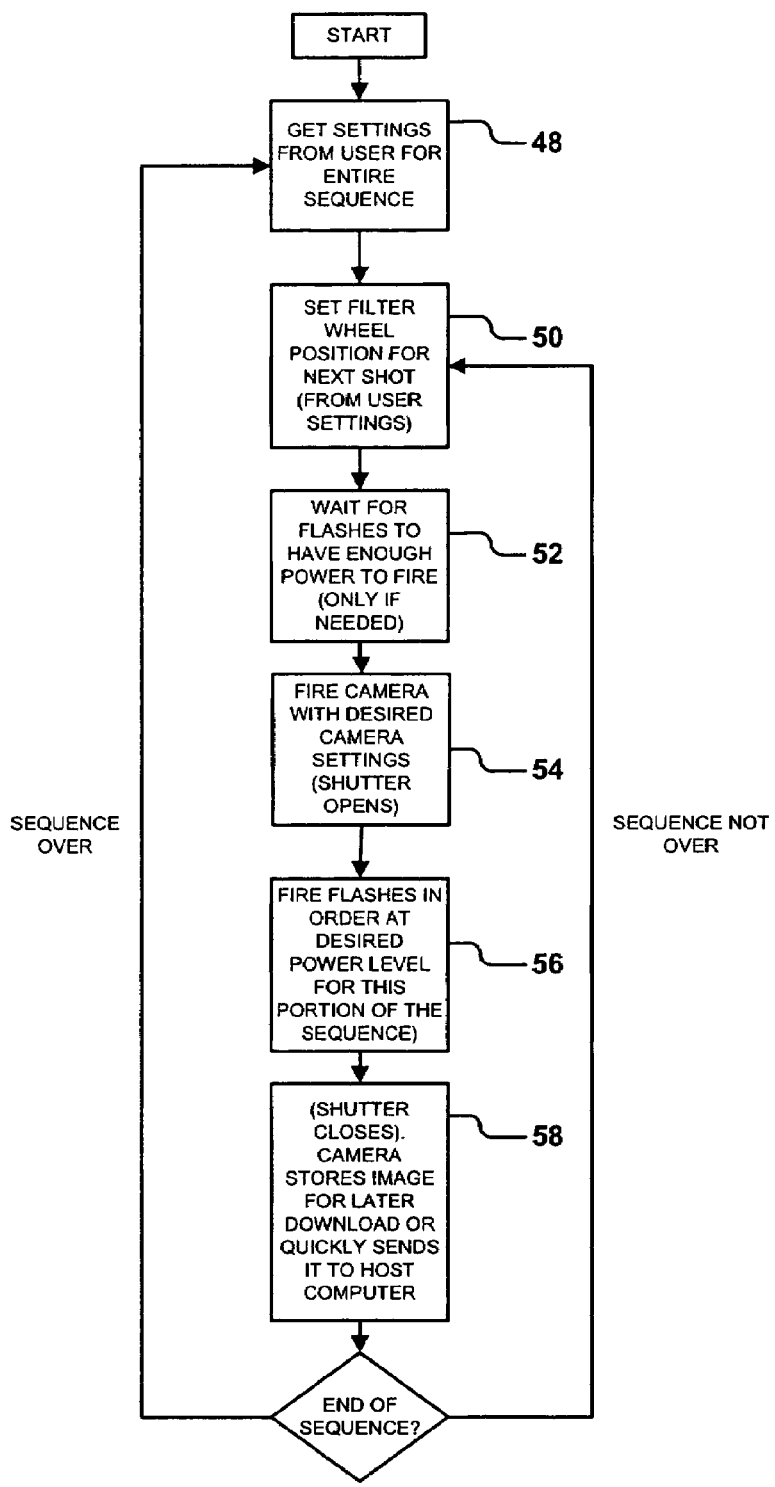
FIG. 4 is a flow chart that describes the operational flow between the user and the invention as well as the internal operations of the invention and its interactions with a camera or other triggering device.

The operation of the system 10 is illustrated in FIG. 4. During the "get settings" section of the first block 48, the user inputs the desired flash and filter settings for each of the frames to be captured. In the second block 50, the invention activates the filter wheel or filter wheels within the camera filter mechanism 44 to place the desired filter for that frame in place. Software control now waits for a calculated amount of time as to allow the flashes to obtain sufficient charge to produce the desired exposure, shown in block 52. It should be noted that any level of charge at or above the desired output level is sufficient to properly fire that flash 36, 38, or 40. The flash will not use any excess charge, as the metering circuit 32 will truncate the light output at the proper exposure level. The camera 42 now takes a picture of the subject with desired camera settings, shown in block 54. While the shutter of the camera 42 is open, all of the flashes programmed to participate in the lighting event sequence fire one at a time, producing their individual requested light output based on feedback from sensor assembly 30, illustrated at box 56. The shutter of the camera 42 now closes and the image is stored in the camera 42 or sent quickly to the host computer, illustrated at box 58. If the frame sequence is over, the system 10 awaits further user input, beginning again at box 48 upon receiving such input. If the frame sequence is not over, the settings for the next frame are loaded and the process begins again from box 50 (filter wheel setup).

Figure 5:
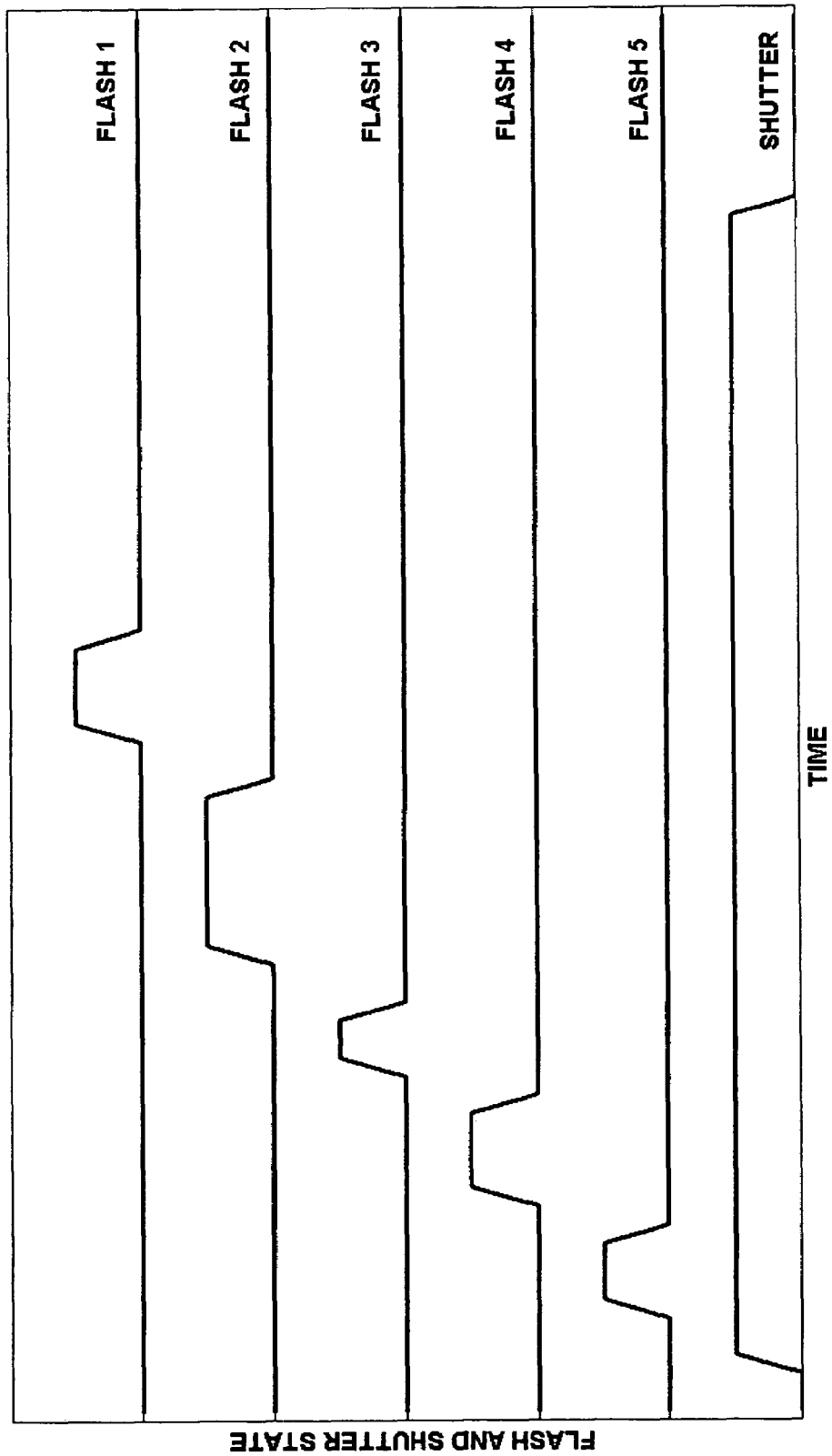
FIG. 5 is a timing diagram that depicts a typical example of a flash firing sequence and the corresponding state of the camera shutter for the present invention.

FIG. 5 depicts a typical example of a flash firing sequence and the corresponding state of the camera shutter where said camera shutter is opened prior to the first flash firing begins and closed alter the last flash firing ends. It also depicts an example of the varying individual flash firing event durations that could be required for that particular flash to produce the desired lighting environment. While a linear firing sequence is illustrated, other firing sequences, such as a random firing sequence, could be used.

Figure 6:
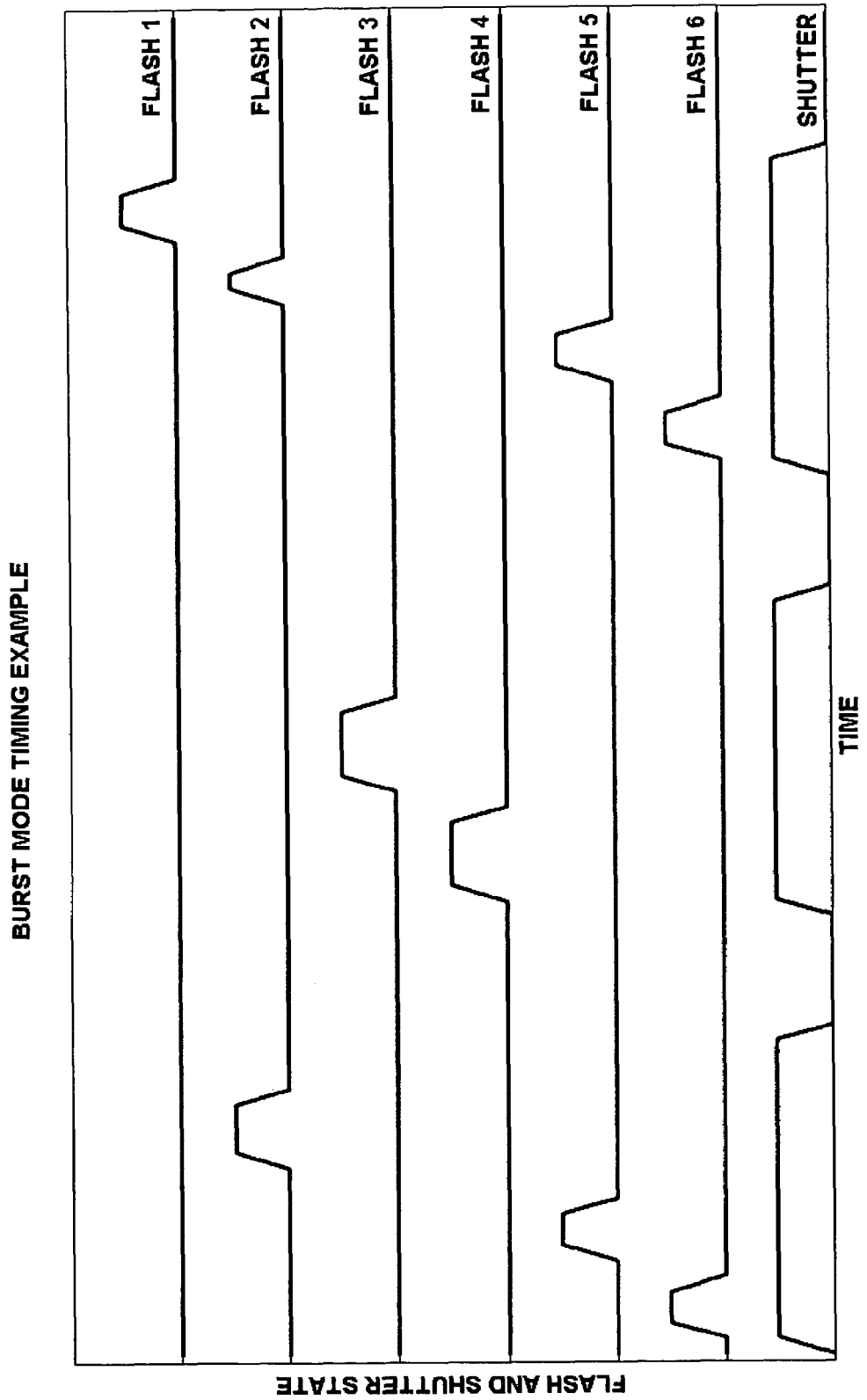
FIG. 6 is a timing diagram that depicts a typical multi-frame flash firing sequence and the corresponding state of the camera shutter.

FIG. 6 depicts a typical multi-frame image capturing sequence and the corresponding state of the camera shutter where said camera shutter is opened prior to each flash sequence, and closed after each sequence. It also depicts an example of the varying individual flash firing events durations that could be required for that particular flash to produce the desired lighting effect for that particular exposure. It should be noted that each time the shutter is closed and then opened again a new frame is captured (and not integrated with the last). It should also be noted that for each frame of capture, a different camera filter can be set in place by the filter mechanism prior to the opening to the shutter but after the previous closing of the shutter.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A photography apparatus, comprising:
   a camera having a lens structured to receive light reflected off of a photographic subject;
   a plurality of light sources structured to illuminate the photographic subject; and
   a control circuit operatively connected to the camera and the plurality of light sources for actuating the plurality of light sources in a predetermined sequence while the camera takes a single photograph of the photographic subject, wherein the control circuit is configured to be programmed to specify which of the plurality of light sources is actuated, along with the timing and sequence of actuation of the actuated light sources, during which at least one of the plurality of light sources is actuated to emit a predetermined power output level and at least one of the plurality of light sources is actuated with a predetermined duration;
   a metering circuit operatively connected to the control circuit, the metering circuit being structured to monitor a light output from the light sources, and to cut-off power to the at least one of the plurality of light sources which is actuated to emit a predetermined power output level upon the light output reaching substantially the predetermined power output level; and
   a structure to house the apparatus including an enclosure for the photographic subject.

2. The photography apparatus according to claim 1, wherein the apparatus is structured to enclose a photographic subject that is a human face or other body part.

3. The photography apparatus according to claim 1, wherein the light sources are selected from the group consisting of flash sources, pulsed-light sources, and continuous-light sources.

4. The photography apparatus according to claim 3, wherein the flash sources include xenon flashes.

5. The photography apparatus according to claim 3 wherein the pulsed-light sources include light emitting diodes.

6. The photography apparatus according to claim 3, wherein the continuous-light sources include those selected from the group consisting of fluorescent, halogen, and tungsten.

7. The photography apparatus according to claim 1, further comprising a filter mechanism disposed either between at least one of the light sources and the photographic subject, or between the photographic subject and the lens of the camera.

8. The photography apparatus according to claim 7, wherein the filter mechanism includes at least one filter selected from the group consisting of polarizing filters and spectrum pass filters.

9. The photography apparatus according to claim 7, wherein the filter mechanism includes multiple filters, and is structured to position a user-selected filter in a location either between at least one of the light sources and the photographic subject, or between the photographic subject and the lens of the camera.

10. The photography apparatus according to claim 1, wherein the control circuit is structured to:
receive desired lighting and filter settings from a user;
determine whether the selected light sources must be charged and charge the selected light sources if necessary;
actuate each selected light source in a user-selected sequence until the metering circuit terminates actuation of each user-selected light source upon light emitted by each light source reaching a user-selected amount.

11. The photography apparatus according to claim 1, wherein the control circuit is further structured to actuate a filter mechanism.

12. The photography apparatus according to claim 11, wherein the control circuit is structured to:
receive desired flash and filter settings from a user;
actuate the filter mechanism to place at least one user-selected filter into an operative position; and
actuate each selected light source in a user-selected sequence until the metering circuit terminates actuation of each user-selected light source upon light emitted by each light source reaches a user-selected amount.

13. The photography apparatus according to claim 1, further comprising a light sensor positioned adjacent to the photographic subject.

14. The photography apparatus according to claim 1, further comprising a sensor assembly structured to be disposed sufficiently close to the photographic subject so that light received by the sensor assembly is substantially the same as the light striking the subject, wherein the metering circuit, in communication with the sensor assembly and the control circuit, is structured to cut-off power to the at least one of the plurality of light sources which is actuated to emit a predetermined power output level upon a luminous flux at the sensor reaching a substantially predetermined level.

15. The photography apparatus according to claim 1, wherein the plurality of light sources includes at least two light sources with different modalities.

16. The photography apparatus according to claim 1, wherein the plurality of light sources includes at least one polarized light source.

17. A photography method, comprising:
providing an enclosure for a photographic subject providing a camera;
providing a plurality of light sources;
providing a control circuit operatively connected to the camera and the plurality of light sources for actuating the plurality of light sources;
programming the control circuit to specify which of the plurality of light sources is actuated, along with the timing and sequence of actuation of the actuated light sources;
actuating the plurality of light sources in a predetermined actuation sequence while the camera takes a single photograph of a photographic subject, during which at least one of the plurality of light sources is actuated to emit a predetermined power output level and at least one of the plurality of light sources is actuated with a predetermined duration;
providing a light sensor in close proximity to the photographic subject;
providing a metering circuit operatively connected to the control circuit and the light sensor; and
terminating electrical power to the at least one of the plurality of light sources which is actuated to emit a predetermined power output level at a time determined by the metering circuit to cause said light source to produce substantially the predetermined power output level.

18. The method according to claim 17, further comprising:
providing a filter mechanism between a photographic subject and either at least one light source or the lens of the camera;
selecting a filter; and
actuating the filter mechanism to position the selected filter between a photographic subject and either at least one light source or the lens of the camera prior to taking a picture.

19. The method according to claim 17, further comprising specifying multiple light source actuation sequences, each light source actuation sequence being for a different photograph.

20. The method according to claim 17, wherein the plurality of light sources includes at least two light sources with different modalities.

21. The method according to claim 17, wherein the plurality of light sources includes at least one polarized light source.

* * * * *